United States Patent [19]
Tsuruhara et al.

[11] Patent Number: 6,060,615
[45] Date of Patent: May 9, 2000

[54] POSITIVELY-CHARGEABLE CHARGE CONTROL AGENT AND TONER FOR DEVELOPING ELECTROSTATIC IMAGES

[75] Inventors: Tohru Tsuruhara, Osaka; Kazuaki Sukata, Kyoto, both of Japan

[73] Assignee: Orient Chemical Industries, Ltd., Japan

[21] Appl. No.: 09/371,240

[22] Filed: Aug. 10, 1999

Related U.S. Application Data

[62] Division of application No. 09/087,754, May 29, 1998.

[30] Foreign Application Priority Data

May 30, 1997 [JP] Japan ..................................... 9-157900

[51] Int. Cl.[7] .............................. C07F 5/06; C07F 15/02; C07F 11/00; G03G 9/097
[52] U.S. Cl. ........................... 556/62; 430/110; 430/120; 556/147; 556/150; 556/184
[58] Field of Search ..................................... 430/110, 120; 556/62, 147, 150, 184

[56] References Cited

U.S. PATENT DOCUMENTS 4,403,027 9/1983 Ishikawa et al. ........................ 430/110
5,232,808 8/1993 Bonser et al. ........................... 430/120

FOREIGN PATENT DOCUMENTS

| 57-119364 | 7/1982 | Japan . |
| 58-98742 | 6/1983 | Japan . |
| 58-186752 | 10/1983 | Japan . |
| 3-1162 | 1/1991 | Japan . |
| 5-100491 | 4/1993 | Japan . |
| 6-11904 | 1/1994 | Japan . |

Primary Examiner—Porfirio Nazario-Gonzalez
Attorney, Agent, or Firm—McGlew and Tuttle, PC

[57] ABSTRACT

Positively-chargeable charge control agent and toner for developing electrostatic images that comprises a coloring agent, a resin for toners, and said positively-chargeable charge control agent. The positively-chargeable charge control agent comprises a metal complex salt or metal complex of an aromatic dicarboxylic acid having at least 1 perfluoroalkyl group, wherein the central atom of the metal complex salt or metal complex is a trivalent metal.

8 Claims, No Drawings

POSITIVELY-CHARGEABLE CHARGE CONTROL AGENT AND TONER FOR DEVELOPING ELECTROSTATIC IMAGES

This is a divisional of application Ser. No. 09/087,754 filed May 29, 1998, now allowed and the entire disclosure of this prior application is considered to be part of the disclosure of the accompanying application and is hereby incorporated by reference therein.

BACKGROUND OF THE INVENTION

1. Field of the Invention

The present invention relates to a toner for developing electrostatic images used in electrophotography etc., and a positively chargeable charge control agent used in said toner for developing electrostatic images etc.

2. Description of the Prior Art

In copying machines, printers and other devices based on electrophotography, various dry or wet toners comprising a coloring agent, a fixing resin and other substances are used to visualize the electrostatic latent image formed on the photoreceptor having a light-sensitive layer containing an organic or inorganic photoconductive substance. There are two types of development processes using dry toners; methods using two-component developers comprising a mixture of a toner and a carrier, and methods using one-component developers comprising a toner used alone without being mixed with a carrier.

development processes using two-component developers include those wherein a toner and a carrier are mixed and subjected to friction to mutually oppositely charge them, after which the charged toner visualizes an oppositely charged electrostatic latent image; specifically magnetic brush development, cascade development, etc. are used according to the kinds of toner and carrier.

One-component development processes include the powder cloud method, wherein toner particles are used in the form of a spray, the impression development process, wherein toner particles are brought into direct contact with the surface of an electrostatic latent image, and the inductive development process, wherein a magnetic electroconductive toner is brought into contact with the surface of an electrostatic latent image.

The chargeability of toners used in various development processes as described above is a key factor in electrostatic latent image-developing systems. Thus, to appropriately control or stabilize toner chargeability, various charge control agents providing a positive or negative charge are added to the toner.

In recent years, as photoconductive materials for the formation of electrostatic latent images in developing systems such as copying machines and laser printers, the consumption of maintenance-free organic photoconductive photoreceptors of low cost and high sensitivity has increased dramatically in the industry. To develop the electrostatic latent image formed on such organic photoconductive photoreceptors, the use of a good positively-chargeable toner is desired. Also, when a conventional selenium photoreceptor is used, the use of a positively-chargeable toner is essential for reversal development.

Of the conventional charge control agents in actual application, those providing a positive charge include basic dyes such as nigrosine dyes and triarylmethane dyes. However, most charge control agents of dye structure are generally structurally complex and unstable; for example, they are likely to be decomposed or deteriorated to lose their initial charge control capability when exposed to mechanical friction or impact, temperature or humidity changes, electric impact, light irradiation, etc. Also, because dyes are chromatic, they lack versatile applicability to color toners, a recently strongly demanded property.

Among positively chargeable charge control agents capable of resolving these problems are the compounds having a nitrogen atom cation in their molecular structure, such as quaternary ammonium salts, iminium salts and pyridinium salts, described in Japanese Patent Unexamined Publication Nos. 119364/1982, 98742/1983, 1162/1991, 100491/1993 and 11904/1994, and the p-halophenylcarboxylic acid described in Japanese Patent Unexamined Publication No. 186752/1983.

Although the positively chargeable charge control agents mentioned here are mostly light-colored and advantageous in that they can be used in color toners, some are unsatisfactory in terms of thermal stability, environmental stability, resin dispersion uniformity, or charge control characteristics, thus calling for further investigation.

The object of the present invention is to provide a positively chargeable charge control agent that has as an active ingredient a metal complex salt or metal complex of new stable chemical structure showing excellent positive charge control characteristics, that is excellent in thermal stability and durability (charge control or enhancement characteristic stability in multiple repeated use), that does not adversely affect toner fixability and offset characteristic when used in a toner, and that is ideal for use in color toners; and a toner for developing electrostatic images that contains said metal complex salt or metal complex as a charge control agent.

SUMMARY OF THE INVENTION

The present inventors found that a metal complex salt or metal complex of an aromatic dicarboxylic acid having at least perfluoroalkyl group as a substituent on the aromatic ring thereof exhibits excellent positive charge control performance, is excellent in heat resistance and durability, is colorless or light-colored, and is ideal as a charge control agent for color toners.

The positively chargeable charge control agent of the present invention is a charge control agent comprising a metal complex salt or metal complex of an aromatic dicarboxylic acid having at least 1 perfluoroalkyl group, wherein the central atom of the metal complex salt or metal complex is a trivalent metal.

This metal complex salt or metal complex of an aromatic dicarboxylic acid has at least 1 perfluoroalkyl group as an aromatic nucleus substituent, as represented by Formula [I] or [II] below.

The toner of the present invention for developing electrostatic images comprises a coloring agent and a resin for toners and contains as a charge control agent a metal complex salt or metal complex of an aromatic dicarboxylic acid having at least 1 perfluoroalkyl group, wherein the central atom of the metal complex salt or metal complex is a trivalent metal.

The positively chargeable charge control agent of the present invention and the toner of the present invention for developing electrostatic images are preferably such that the above-described metal complex salt or metal complex of an aromatic dicarboxylic acid is represented by Formula [I] or [II] below. In Formula [II], 3 moles of ligand aromatic dicarboxylic acid are coordinated to 2 moles of metal M.

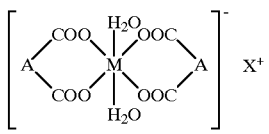

[I]

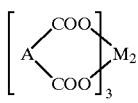

[II]

In Formulas [I] and [II],
A represents

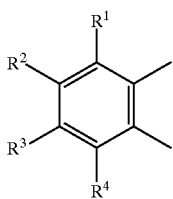

or

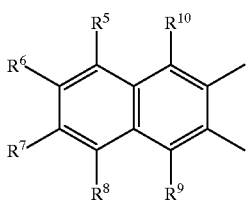

M represents a trivalent metal;

$X^+$ represents $H^+$, an alkal metal cation, $NH^+_4$, a cation based on an organic amine, or a quaternary organic ammonium ion.

In the former formula, each of $R^1$, $R^2$, $R^3$ and $R^4$ independently represents hydrogen (H) or a linear or branched perfluoroalkyl group, but not all of $R^1$ through $R^4$ are hydrogen (H).

In the latter formula, each of $R^5$, $R^6$, $R^7$, $R^8$, $R^9$ and $R^{10}$ independently represents hydrogen (H) or a linear or branched perfluoroalkyl group, but not all of $R^5$ through $R^{10}$ are hydrogen.

Also, the positively chargeable charge control agent of the present invention and the toner of the present invention for developing electrostatic images are preferably such that the above-described trivalent metal is a metal selected from the group consisting of Al, Fe and Cr.

In addition, the positively chargeable charge control agent of the present invention and the toner of the present invention for developing electrostatic images are preferably such that the carbon number of the above-described perfluoroalkyl group is an integer from 1 to 8.

The positively-chargeable charge control agent of the present invention, especially one containing as an active ingredient an aromatic dicarboxylic acid metal complex salt or metal complex represented by Formula [I] or [II], is well dispersible in resins, possess excellent charge control characteristics, is excellent in thermal stability and durability, and does not adversely affect toner fixability and offset characteristic when used in toners. Even when the positively-chargeable charge control agent of the present invention is used in a toner together with a weakly negatively-chargeable resin such as polyester resin, the resulting toner exhibits stable and good positive charge characteristics. Also, because the positively-chargeable charge control agent of the present invention is colorless or light-colored, it is unlikely to cause color tone damage when used in various toners and electrostatic resin powders, and is therefore ideal for use in color toners. Furthermore, the positively-chargeable charge control agent of the present invention is also suited for use in frictional charge-providing elements that provide a negative charge for a toner.

The toner of the present invention for developing electrostatic images is excellent in charge stability, environmental resistance, storage stability, thermal stabilityl and durability, and good in fixability and offset characteristic. Also, because the metal complex salt or metal complex contained as a charge control agent is colorless or light-colored, color tone damage in toner images is unlikely.

DETAILED DESCRIPTION OF THE INVENTION

With respect to the metal complex salt or metal complex of an aromatic dicarboxylic acid in the present invention, the central atom to which the ligand is coordinated is a trivalent metal. Examples of such metals include Al, Fe, Cr, Ni, Co, Ti, Mn and Mo. Preferable trivalent metals are Al, Fe and Cr, with greater preference given to Al.

The perfluoroalkyl group present as an aromatic nucleus substituent in the aromatic dicarboxylic acid in the present invention may be linear or branched. The carbon number of this perfluoroalkyl group is preferably 1 to 8, more preferably 1 to 4.

The perfluoroalkyl group in the present invention is exemplified by trifluoromethyl group,
pentafluoroethyl group,
n-heptafluoropropyl group,
isoheptafluoropropyl group,
n-nonafluorobutyl group,
isononafluorobutyl group,
sec-nonafluorobutyl group,
tert-nonafluorobutyl group,
n-tridecafluorohexyl group,
n-heptadecafluorooctyl group and
tert-heptadecafluorooctyl group.

The aromatic dicarboxylic acid in the present invention is exemplified by perfluoroalkyl-substituted phthalic acids such as
3-trifluoromethylphthalic acid,
4-trifluoromethylphthalic acid,
2-pentafluoroethylphthalic acid,
3-pentafluoroethylphthalic acid,
4-pentafluoroethylphthalic acid,
3-isoheptafluoropropylphthalic acid,
3-tert-nonafluorobutylphthalic acid,
3-n-tridecafluorohexylphthalic acid,
4-trifluoromethyl-3-tert-nonafluorobutylphthalic acid,
3,4-di-trifluoromethylphthalic acid,
3-trifluoromethyl-5-pentafluoroethylphthalic acid,
3,5-di-trifluoromethylphthalic acid,
3,5-di-tert-nonafluorobutylphthalic acid, 3-tert-nonafluorobutyl-5-isoheptafluoropropylphthalic acid, 3-isoheptadecafluorooctylphthalic acid and 3-tert-heptadecafluorooctylphthalic acid; and perfluoroalkyl-substituted naphthalenedicarboxylic acids such as 6-trifluoromethyl-2,3-naphthalenedicarboxylic acid, 6-pentafluoroethyl-2,3-naphthalenedicarboxylic acid, 6-tert-nonafluorobutyl-2,3-naphthalenedicarboxylic acid, 6-n-heptafluoropropyl-2,3-naphthalenedicarboxylic acid, 6-tert-nonafluorobutyl-2,3-naphthalenedicarboxylic acid, 6-tert-heptadecafluorooctyl-2,3-naphthalenedicarboxylic acid, 5,7-di-trifluoromethyl-2,3-naphthalenedicarboxylic acid, 5,7-di-tert-nonafluorobutyl-2,3-naphthalenedicarboxylic acid, 5-trifluoromethyl-7 n-heptafluoropropyl-2,3-naphthalenedicarboxylic acid, 6-trifluoromethyl-1,2-naphthalenedicarboxylic acid, 6-pentafluoroethyl-1,2-naphthalenedicarboxylic acid, 7-pentafluoroethyl-1,2-naphthalenedicarboxylic acid, 7-n-tridecafluorohexyl-1,2-naphthalenedicarboxylic acid, 7-isoheptafluoropropyl-1,2-naphthalenedicarboxylic acid, 5,7-di-trifluoromethyl-1,2-naphthalenedicarboxylic acid and 5-trifluoromethyl-7-n-heptafluoropropyl-1,2-naphthalenedicarboxylic acid.

The metal complex salt or metal complex of an aromatic dicarboxylic acid in the present invention can be obtained by chelating the aromatic dicarboxylic acid by a known method. For example, it can be obtained by dissolving a perfluoroalkyl aromatic dicarboxylic acid as described above in an alkali added in a sufficient amount, adding a metallizing agent to the solution in an amount resulting in a metal perfluoroalkyl aromatic dicarboxylic acid molar ratio of 1:2 or 2:3, heating the mixture, collecting the resulting precipitate by filtration, and washing it.

Metallizing agents that can be used to produce the metal complex salt or metal complex of an aromatic dicarboxylic acid in the present invention include, for example, aluminum compounds such as aluminum sulfate, aluminum chloride, poly(aluminum chloride) and aluminum nitrate; iron compounds such as ferric chloride, ferric sulfate and ferric nitrate; and chromium compounds such as chromium sulfate, chromium chloride, chromium acetate and chromium formate.

Examples of the counter-ion ($X^+$) for the aromatic dicarboxylic acid metal complex salt represented by Formula [I] above include $H^+$, cations based on alkali metals (Na, K, etc.), $NH^+_4$, cations based on organic amines (aliphatic primary amines, aliphatic secondary amines, aliphatic tertiary amines, etc.) and quaternary organic ammonium ions.

The metal complex salt or metal complex of an aromatic dicarboxylic acid in the present invention is exemplified by the compounds shown below.

Example Compound 1

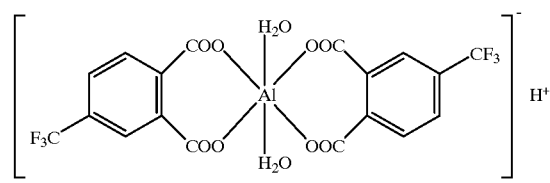

Example Compound 2

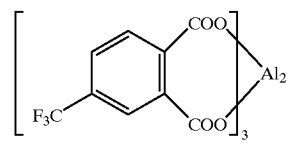

Example Compound 3

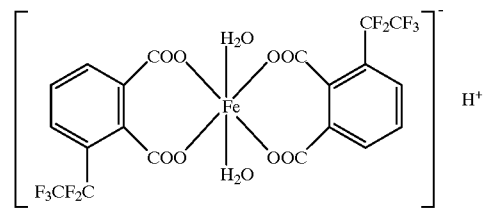

Example Compound 4

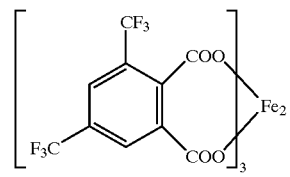

Example Compound 5

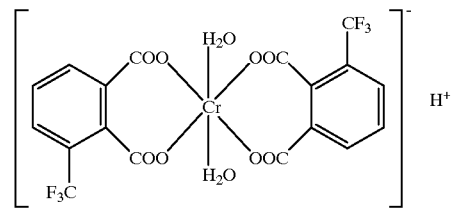

Example Compound 6

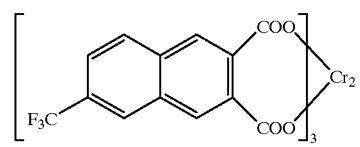

Example Compound 7
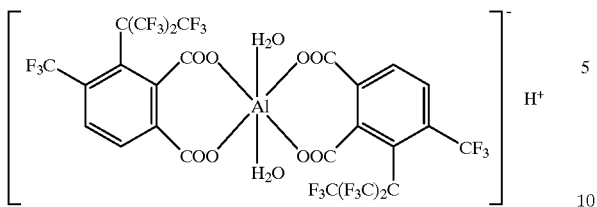
Example Compound 12
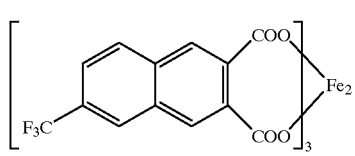
Example Compound 8
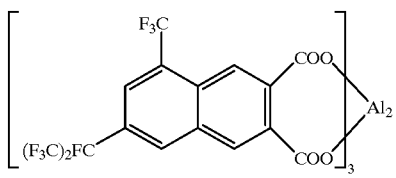
Example Compound 13
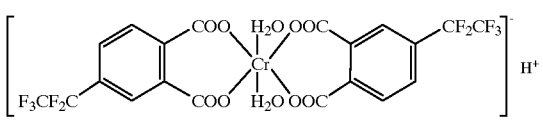
Example Compound 9
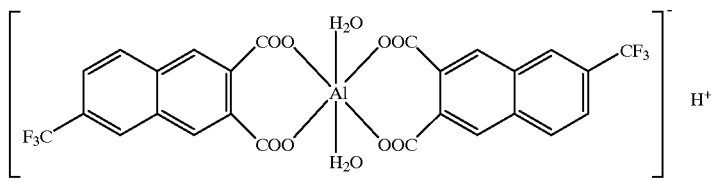
Example Compound 14
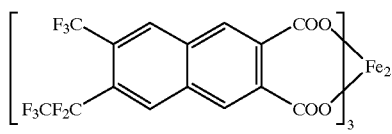
Example Compound 10
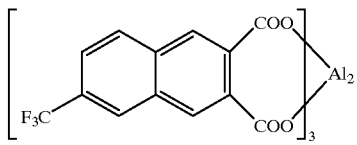
Example Compound 15
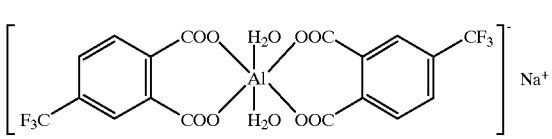
Example Compound 11
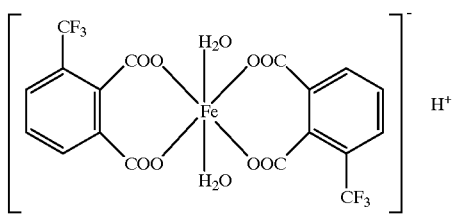
Example Compound 16
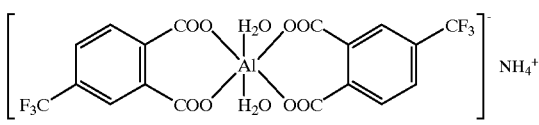

Example Compound 17

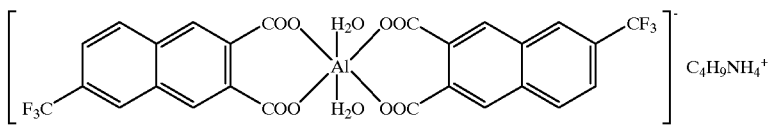

The charge control agent in the present invention is preferably an aromatic dicarboxylic acid metal complex salt or metal complex represented by Formula [I] or [II] above, which is well dispersible in resins for toners.

The toner of the present invention for developing electrostatic images incorporates the charge control agent of the present invention in an amount suited for toner charge control. Preferable amounts of charge control agent added are 0.1 to 10 parts by weight per 100 parts by weight of resin, more preferably 0.5 to 5 parts by weight per 100 parts by weight of resin. The toner of the present invention for developing electrostatic images may incorporate 1 or more kinds of this aromatic dicarboxylic acid metal complex salt or metal complex as a charge control agent. Also, the charge control agent of the present invention may concurrently contain other positively chargeable charge control agents in traditional use, such as light-colored quaternary ammonium salts, as long as the accomplishment of the intended object is not interfered with.

Examples of resins useful in the toner of the present invention include the following known resins for toners (binder resins). Specifically, useful resins include styrene resin, styrene-acrylic resin, styrene-butadiene resin, styrene-maleic acid resin, styrene- vinyl methyl ether resin, styrene-methacrylic ester copolymer, phenol resin, epoxy resin, polyester resin, polypropylene resin and paraffin wax. These resins may be used singly or in blends.

In the toner of the present invention, various dyes and pigments can be used as coloring agents. Examples of useful coloring agents include organic pigments such as Quinophthalone Yellow, Isoindolinone Yellow, Perynone Orange, Perylene Maroon, Rhodamine 6G Lake, Quinacridone Red, Rose Bengale, Copper Phthalocyanine Blue, Copper Phthalocyanine Green and diketopyrrolopyrrole pigments; inorganic pigments such as Carbon Black, Titanium White, Titanium Yellow, Ultramarine, Cobalt Blue and iron oxide red; various oil-soluble dyes and disperse dyes such as azo dyes, quinophthalone dyes, anthraquinone dyes, phthalocyanine dyes, indophenol dyes and indoaniline dyes; and triarylmethane dyes and xanthene dyes modified with resins such as rosin, rosin-modified phenol and rosin-modified maleic acid.

In the toner of the present invention for developing electrostatic images, the above-mentioned coloring agents can be used singly or in combination of 2 or more kinds. Chromatic monocolor toners can incorporate as coloring agents appropriately mixed dyes and pigments of the same color, e.g., quinophthalone dyes and pigments, xanthene or rhodamine dyes and pigments, and phthalocyanine dyes and pigments.

Also, to improve toner quality, additives, e.g., electroconductive particles, fluidity-improving agents and image peeling inhibitors, can be added to the toner internally or externally.

The toner of the present invention for developing electrostatic images can, for example, be produced as described below. For example, a toner having an average particle diameter of 1 to 15 μm can be obtained by thoroughly mixing a resin for toners, a coloring agent, and the charge control agent of the present invention as described above, and, if necessary, a magnetic material, a fluidizing agent and other additives, using a ball mill or another mechanical mixer, subsequently kneading the mixture in a molten state using a hot kneader such as a heat roll, kneader or extruder, cooling and solidifying the mixture, then pulverizing the solid and classifying the resulting particles by size.

Other applicable methods include the method in which other starting materials are dispersed in a binder resin solution and subsequently spray dried to yield the desired toner, and the polymerizing toner production method in which a given set of starting materials are mixed in a monomer to constitute a binder resin to yield an emulsified suspension, which is then polymerized to yield the desired toner.

When the toner of the present invention for developing electrostatic images is used as a two-component developer, development can be achieved by the two-component magnetic brush development process or the like using the toner in mixture with carrier powder.

Any known carrier can be used. Examples of the carrier include iron powder, nickel powder, ferrite powder and glass beads about 50 to 200 μm in particle diameter, and such materials as coated with acrylic ester copolymer, styrene-acrylic ester copolymer, styrene-methacrylic ester copolymer, silicone resin, polyamide resin, ethylene fluoride resin or the like.

When the toner of the present invention for developing electrostatic images is used as a one-component developer, an appropriate amount of fine powder of a ferromagnetic material such as iron powder, nickel powder or ferrite powder may be added and dispersed in preparing the toner as described above.

On the other hand, by adding the positively-chargeable charge control agent of the present invention to a positively-chargeable resin powder paint for electrostatic painting, the charge of the powder paint can be controlled or enhanced. Because resin powder paints for electrostatic painting containing the positively-chargeable charge control agent of the present invention are excellent in heat resistance and good in positive charge enhancing characteristic, they exhibit high paint adhesion efficiency, thus minimizing the necessity for the recycled use of the powder paint. Painting using such powder paints can be achieved by ordinary electrostatic powder painting methods such as the corona application method, the frictional chargeable method and the hybrid method.

It is also possible to obtain a frictional charge-providing element capable of providing a negative charge for a toner for developing electrostatic images by coating the surface of a transportation element for a carrier and a toner, such as a cylindrical sleeve or a doctor blade, with a metal complex salt or metal complex of an aromatic dicarboxylic acid having a perfluoroalkyl group, which metal complex salt or metal complex serves as the positively-chargeable charge control agent of the present invention, by dipping, spraying, brush application or the like.

The aromatic dicarboxylic acid metal complex salt or metal complex used for this frictional charge-providing element is capable of stably providing a negative charge for a toner and producing toner images of high quality comparable to that of initial images even after continuous copying. Also, this frictional charge-providing element may concurrently contain a small amount of an auxiliary negative charge-providing agent (e.g., quaternary ammonium salt type etc.).

EXAMPLES

The present invention is hereinafter described in more detail by means of Examples 1 through 8, which pertain to toners for developing electrostatic images containing the charge control agent of the present invention, but which are not to be construed as limitative. In the description below, "part(s) by weight" is referred to as "part(s)" for short.

Example 1

Styrene-acrylic copolymer resin [trade name: HIMER SMB600, produced by Sanyo Kasei Co., Ltd.] . . . 100 parts Carbon Black [trade name: RAVEN1250, produced by Columbia Carbon Co., Ltd.] . . . 8 parts Charge control agent (Example Compound 2) . . . 1 part The above ingredients were uniformly pre-mixed using a ball mill to yield a premix, which was then kneaded in a molten state using a heat roll, cooled and thereafter roughly milled using a vibration mill. The rough milling product obtained was finely pulverized using an air jet mill equipped with a classifier to yield a positively-chargeable black toner 5 to 15 μm in particle diameter.

Three parts of this toner was admixed with 97 parts of an iron powder carrier [trade name: TEFV200/300, produced by Powdertech Co., Ltd.) to yield a developer. The amount of initial blowoff charges of this developer was +24.3 μC/g. After 10,000 copies were taken using a copying machine incorporating a toner-recycling apparatus, the amount of blowoff charges was +23.8 μC/g, demonstrating that the amount of blowoff charges of this developer was very stable.

When this toner was used to form toner images using a commercial copying machine, fogging-free high-quality black images with good thin line reproducibility were obtained. Even after 20,000 copies were continuously taken, good black images were obtained with no image density reduction or offset phenomenon.

Example 2

A toner and a developer were prepared and evaluated in the same manner as in Example 1, except that the charge control agent used in Example 1 (Example Compound 2) was replaced with Example Compound 1. The amount of initial blowoff charges of this developer was +23.7 μC/g. When this developer was used for repeated cycles of actual imaging in the same manner as in Example 1, high-quality images free of image density reduction and fogging were obtained, with good charge stability and sustainability and no offset phenomenon.

Example 3

A toner and a developer were prepared and evaluated in the same manner as in Example 1, except that the charge control agent used in Example 1 (Example Compound 2) was replaced with Example Compound 4. The amount of initial blowoff charges of this developer was +16.8 μC/g. When this developer was used for repeated cycles of actual imaging in the same manner as in Example 1, high-quality images free of image density reduction and fogging were obtained, with good charge stability and sustainability and no offset phenomenon.

Example 4

A toner and a developer were prepared and evaluated in the same manner as in Example 1, except that the charge control agent used in Example 1 (Example Compound 2) was replaced with a mixture of Example Compound 1 and Example Compound 2. The amount of initial blowoff charges of this developer was +23.0 μC/g. When this developer was used for repeated cycles of actual imaging in the same manner as in Example 1, high-quality images free of image density reduction and fogging were obtained, with good charge stability and sustainability and no offset phenomenon.

Comparative Example 1

A black toner was prepared in the same manner as in Example 1, except that the charge control agent used in Example 1 (Example Compound 2) was replaced with a compound represented by Formula [III] below:

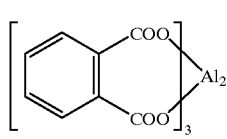

[III]

When this toner was used to prepare a developer in the same manner as in Example 1, and the amount of initial blowoff charges of this developer was determined, the desired amount of positive charges was not obtained. When this toner was used to form toner images, considerable fogging occurred.

Comparative Example 2

A black toner was prepared in the same manner as in Example 1, except that the charge control agent used in Example 1 (Example Compound 2) was replaced with a compound represented by Formula [IV] below:

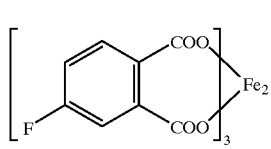

[IV]

When this toner was used to prepare a developer in the same manner as in Example 1, and the amount of initial blowoff charges of this developer was determined, the desired amount of positive charges was not obtained. When this toner was used to form toner images, considerable fogging occurred.

Comparative Example 3

A black toner was prepared in the same manner as in Example 1, except that the charge control agent used in Example 1 (Example Compound 2) was replaced with a compound represented by Formula [V] below:

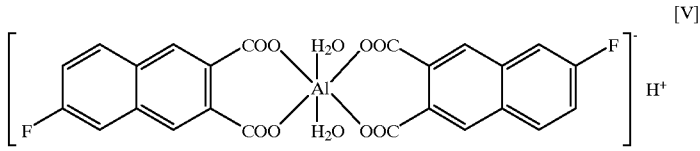

When this toner was used to prepare a developer in the same manner as in Example 1, and the amount of initial blowoff charges of this developer was determined, the desired amount of positive charges was not obtained. When this toner was used to form toner images, considerable fogging occurred.

Example 4

Styrene-acrylic copolymer resin (trade name: HIMER SMB600, produced by Sanyo Kasei Co., Ltd.] . . . 100 parts Copper Phthalocyanine pigment . . . 6 parts Charge control agent (Example Compound 2) . . . 2 parts The above ingredients were treated in the same manner as in Example 1 to yield a blue toner.

A developer was prepared in the same manner as in Example 1; the amount of initial blowoff charges of this developer was determined to be +19.9 µC/g. After 10,000 copies were taken using a copying machine incorporating a toner-recycling apparatus, the amount of blowoff charges of this developer was determined to be +19.5 µC/g, demonstrating that the amount of blowoff charges of this developer was very stable.

When this toner was used to form toner images using a commercial copying machine, fogging-free high-quality blue images with good thin line reproducibility were obtained. Even after 20,000 copies were continuously taken, good blue images were obtained with no image density reduction or offset phenomenon.

Example 5

A toner and a developer were prepared and evaluated in the same manner as in Example 4, except that the charge control agent used in Example 4 (Example Compound 2) was replaced with Example Compound 4. The amount of initial blowoff charges of this developer was +16.7 µC/g. When this developer was used for repeated cycles of actual imaging in the same manner as in Example 4, high-quality images free of image density reduction and fogging were obtained, with good charge stability and sustainability and no offset phenomenon.

Example 6

A toner and a developer were prepared and evaluated in the same manner as in Example 4, except that the charge control agent used in Example 1 (Example Compound 2) was replaced with a mixture of Example Compound 2 and Example Compound 4. The amount of initial blowoff charges of this developer was +20.0 µC/g. When this developer was used for repeated cycles of actual imaging in the same manner as in Example 4, high-quality images free of image density reduction and fogging were obtained, with good charge stability and sustainability and no offset phenomenon.

Comparative Example 4

A blue toner was prepared in the same manner as in Example 4, except that the charge control agent used in Example 4 (Example Compound 2) was replaced with a compound represented by Formula [VI] below:

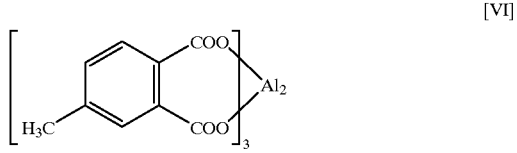

When this toner was used to prepare a developer in the same manner as in Example 4, and the amount of initial blowoff charges of this developer was determined, the desired amount of positive charges was not obtained. When this toner was used to form toner images, considerable fogging occurred.

Example 7

Styrene resin [trade name: Vicolastic D-125, produced by Esso Sekiyu Co., Ltd.] . . . 100 parts Low polymer polypropylene [trade name: Biscal 550P, produced by Sanyo Kasei Co., Ltd.] . . . 10 parts Phthalocyanine Green pigment . . . 7 parts Charge control agent (Example Compound 6) . . . 3 parts The above ingredients were treated in the same manner as in Example 1 to yield a green toner.

A developer was prepared in the same manner as in Example 1; the amount of initial blowoff charges of this developer was determined to be +23.1 µC/g. After 10,000 copies were taken using a copying machine incorporating a toner-recycling apparatus, the amount of blowoff charges was determined to be +22.8 µC/g, demonstrating that the amount of blowoff charges of this developer was very stable.

When, this toner was used to form toner images using a commercial copying machine, fogging-free high-quality green images with good thin line reproducibility were obtained. Even after 20,000 copies were continuously taken, good green images were obtained with no image density reduction or offset phenomenon.

Example 8

A toner and a developer were prepared and evaluated in the same manner as in Example 7, except that the charge control agent used in Example 7 (Example Compound 6) was replaced with Example Compound 1. The amount of initial blowoff charges of this developer was +22.4 µC/g. When this developer was used for repeated cycles of actual imaging in the same manner as in Example 7, high-quality images free of image density reduction and fogging were obtained, with good charge stability and sustainability and no offset phenomenon.

What is claimed is:

1. Positively-chargeable charge control agent comprising a metal complex salt or metal complex of an aromatic dicarboxylic acid having at least 1 perfluoroalkyl group, wherein the central atom of the metal complex salt or metal complex is a trivalent metal.

2. Positively-chargeable charge control agent of claim 1 wherein said metal complex salt or metal complex of an aromatic dicarboxylic acid is represented by Formula [I] or [II] below:

[I]

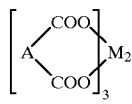

[II]

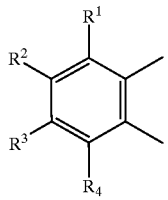

In Formulas [I] and [II],

A represents

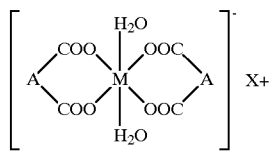

or

-continued

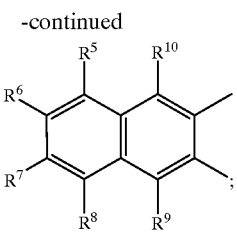

M represents a trivalent metal;

$X^+$ represents $H^+$, an alkali metal cation, $NH^+_4$, a cation based on an organic amine, or a quaternary organic ammonium ion;

In the former formula, each of $R^1$, $R^2$, $R^3$ and $R^4$ independently represents hydrogen or a linear or branched perfluoroalkyl group, except that not all of $R^1$ through $R^4$ are hydrogen;

In the latter formula, each of $R^5$, $R^6$, $R^7$, $R^8$, $R^9$ and $R^{10}$ independently represents hydrogen or a linear or branched perfluoroalkyl group, except that not all of $R^5$ through $R^{10}$ are hydrogen.

3. Positively-chargeable charge control agent of claim 1 wherein said trivalent metal is a metal selected from the group consisting of Al, Fe and Cr.

4. Positively-chargeable charge control agent of claim 2 wherein said trivalent metal is a metal selected from the group consisting of Al, Fe and Cr.

5. Positively-chargeable charge control agent of claim 1 wherein the carbon number of said perfluoroalkyl group is an integer of 1 to 8.

6. Positively-chargeable charge control agent of claim 2 wherein the carbon number of said perfluoroalkyl group is an integer of 1 to 8.

7. Positively-chargeable charge control agent of claim 3 wherein the carbon number of said perfluoroalkyl group is an integer of 1 to 8.

8. Positively-chargeable charge control agent of claim 4 wherein the carbon number of said perfluoroalkyl group is an integer of 1 to 8.

* * * * *